US005435318A

United States Patent [19]

Silverman

[11] Patent Number: 5,435,318

[45] Date of Patent: Jul. 25, 1995

[54] BRIDLE TENSION INDICATOR DEVICE

[76] Inventor: Simeon A. Silverman, 19 Lake View, Edgware, Middlesex HA8 7RT, England

[21] Appl. No.: 955,747

[22] PCT Filed: Jun. 7, 1991

[86] PCT No.: PCT/GB91/00916

§ 371 Date: Dec. 15, 1992

§ 102(e) Date: Dec. 15, 1992

[87] PCT Pub. No.: WO91/19667

PCT Pub. Date: Dec. 26, 1991

[30] Foreign Application Priority Data

Jun. 15, 1990 [GB] United Kingdom ................ 9013461

[51] Int. Cl.[6] ............................................ A61B 5/103

[52] U.S. Cl. .................................................... 128/774

[58] Field of Search .............................. 128/774, 782; 33/511-514

[56] References Cited

U.S. PATENT DOCUMENTS

| | | | |
|---|---|---|---|
| 4,846,462 | 7/1989 | Regnier et al. | 128/782 |
| 4,871,998 | 10/1989 | Chaillou | 128/782 |
| 4,914,423 | 4/1990 | Fernandez | 128/782 |
| 4,938,476 | 7/1990 | Brunelle et al. | 128/782 |
| 5,507,294 | 4/1991 | Matjasic . | |

FOREIGN PATENT DOCUMENTS 1600881 10/1981 United Kingdom .

*Primary Examiner*—Max Hindenburg

*Attorney, Agent, or Firm*—Ladas & Parry

[57] ABSTRACT

A bridle tension indicator device with which the invention is concerned is to be connectable to one or both reins (R) of a bridle for a horse. The device includes an electrical circuit responsive to the tension in the reins (R) so that when the tension exceeds a selectible predetermined value an electrical signal is generated. The signal is used to illuminate a lamp (8) or alternatively give an audible warning from an audio signal emitting device (11) either in the form of a continuous tone, or a synthesized voice instruction. Conveniently, the electrical circuit is housed in a two part housing (1), with the two parts (2,3) being slidable one relative to the other. The housing parts are preferably biased to a closed position by a spring. Accordingly, the indicator device assists in improvement of a rider's control of a horse. Moreover, the control of the horse is further affected by ensuring correct posture when sitting on a horse such as by modifying the indicator device above to operate in response to a switch activated by a deviation from a horizontal or vertical plane. A time delay circuit is preferably included to prevent operation in response to momentary changes.

11 Claims, 2 Drawing Sheets

BRIDLE TENSION INDICATOR DEVICE

This invention relates to a bridle tension indicator device.

When riding a horse signals for instructing to the horse to perform various acts such as turning in a particular direction, slowing down or stopping are transmitted through the bridle as well as the rider's seat, knee or heel pressure against the horse body.

When a rider is inexperienced at horse riding there is an instinctive tendency for a rider to pull heavily upon the reins to turn or stop the horse even though such action may not actually be necessary in the circumstances prevailing at a particular time. The result of unduly hard pulling on the reins is to pull the bridle bit which is located in the horse's mouth forcefully against the corners of the horse's mouth, in some cases damaging the mouth to such an extent that eventually the mouth becomes insensitive to such instruction leading to the reins being pulled harder to obtain the desired result. This is due to the fact that the rider has not learned that the required signal, for any transition, in a schooled horse, is that of the Half Halt. This is simply a taking and giving of the rein, that may involve no more than a slight closing of the fingers. Together with the use of the back and lumber muscles pushing the seat towards the pommel of the saddle.

It is therefore desirable to provide a device which will assist in teaching a rider how to control the movement of a horse using the reins correctly, and thereby substantially reduce damage to a horse's mouth.

According to one aspect of the present invention there is provided a bridle tension indicator device connectible to a rein of the bridle, characterised in an electric circuit for producing a signal when the tension in the reins exceeds a predetermined amount, switch for initiating operation of the electrical circuit, and an indicator for providing indication that the predetermined tension has been exceeded in response to a signal emitted by the electrical circuit means.

In one preferred embodiment of the invention the indicator device is arranged to emit an audible signal which may be a continuous tone, or alternatively, a synthesized voice instruction. In a further embodiment the indicator may be an indicator lamp which lights up when the predetermined tension is surpassed. The indicator device can be provided with one or both audio/-visual indicators, and may also have a liquid crystal display to clearly indicate the timing programme that has been set.

In one preferred form of the invention the indicator device includes a housing in two parts one slidable relative to the other so that when attached to the reins and the reins are pulled straight the parts of the housing are moved apart and cause the indicator circuit to provide the indicator signal. The parts of the housing are biased to a closed position, preferably by a spring the tension in which is adjustable. Conveniently, the indicator device is attached to the reins by threading the reins about a plurality of bars on either part of the housing, or alternatively, by studs or simply loops.

According to another aspect of the present device there is provided a constant level indicator device arranged to be attached to a selected part of a person's anatomy, the device being characterised in an electrical circuit for producing an electrical signal representative of the said deviation from the horizontal or vertical plane, a switch operable in response to the said deviation from a horizontal or vertical plane for initiating operation of the electrical circuit, and an indicator for providing a signal indicative of a deviation from the said horizontal or vertical plane.

In an alternative form of the invention the indicator device includes a housing in two elongate hollow parts one pivotally mounted relative to the other at one end of those parts with a biasing spring attachable between free ends of the elongate parts opposite to the interconnected ends thereof.

In either embodiment the biasing spring biases the indicator device to a closed position thereof and in this position the reins attached to the device are preferably provided with a slight loop between the attachments thereof on opposite sides of the device, thus allowing a certain amount of movement prior to initiating a warning signal by operation of the electrical circuit therein. The device may also be included as part of a ready to use rein.

Embodiments of the present invention will now be described by way of example with reference to the accompanying drawings, in which.

Figure 1:
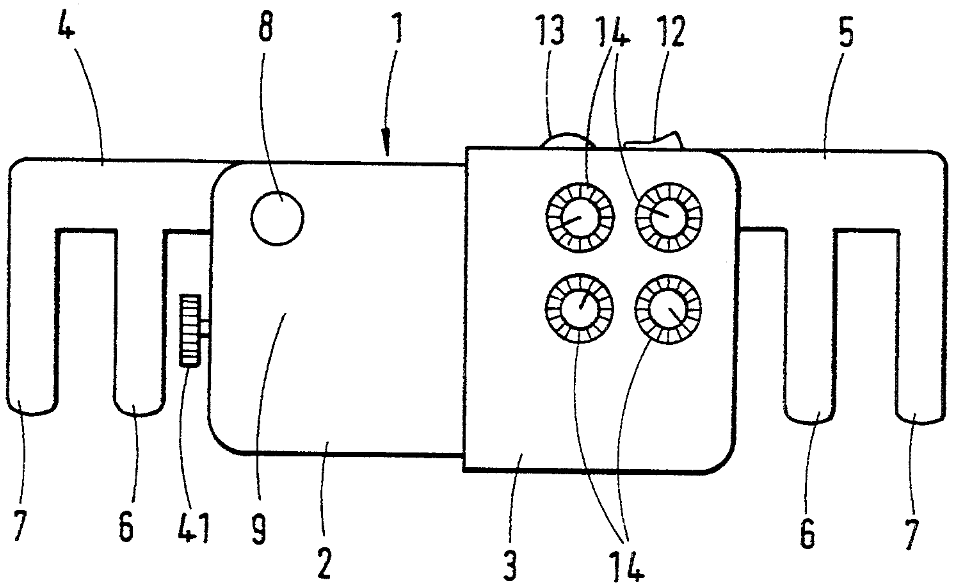
FIG. 1 is a side elevational view of one indicator device according to the invention.
Figure 2:
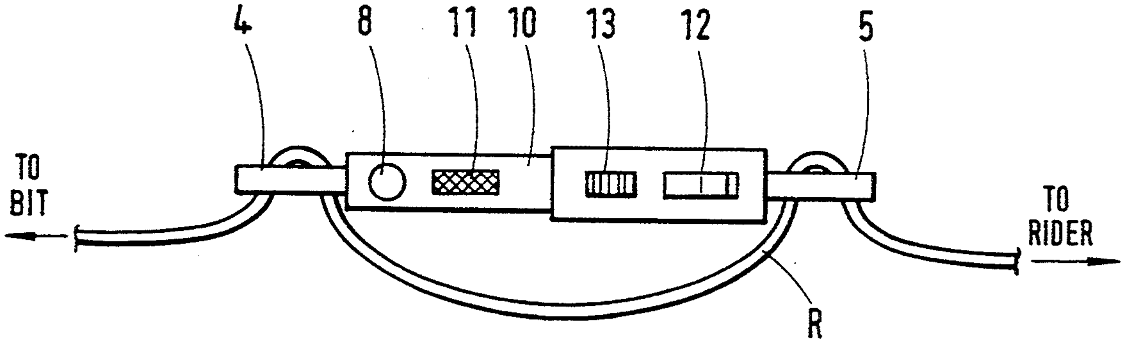
FIG. 2 is a top view of a modified form of the device of FIG. 1.

Referring to FIGS. 1 and 2 there is disclosed a bridle tension indicator device comprising a housing 1 having two relatively slidable interengageable parts 2, 3 within which are housed an electrical circuit (not shown) for generating an indicator signal.

The housing parts 2, 3 are each provided with an elongate lug 4, 5 extending outwardly from the housing part 2, 3 in a direction corresponding to the mutually opposed directions of movement of the housing parts one relative to the other. Each lug 4, 5 is provided with two spaced transversely extending bar-like projections 6, 7. The space between the projections 6, 7 and the space between the projection 6 and the corresponding housing part 2, 3 is used to receive one rein R of a bridle with a loop to one side of the housing between opposed groups of the projections 6, 7 as shown in FIG. 2.

The electrical circuit used to generate a tension indicator signal can be any conventional circuit for generating a signal which incorporates a time delay, set with a variable capacitor, and which is convertible into a visual or audible signal and therefore will not be discussed further in this disclosure.

The signal generated by the electrical circuit within the housing can be conveniently directed to a lamp 8 to illuminate, or alternatively switch off the lamp when the tension in the reins exceeds a predetermined value. The lamp 8 is conveniently located either on one side 9 of one part 2 of the main housing, or alternatively, as shown in FIG. 2 along top surface 10 of the housing part 2. An audio signal emitting device 11 may be similarly located on the side surface 9 adjacent the visual indicator lamp 8 of FIG. 1, or alternatively, on the top surface as shown in FIG. 2. An on/off switch 12 can also be provided on the top surface 10 of housing part 3 to activate the device, whilst a volume control 13 is similarly provided on the top surface 10 to control the volume of an audio signal emission from the audio signal emitting device.

Conveniently, the bridle tension indicator device is provided with various rotary or slidable control knobs or push buttons with appropriate seals as appropriate on the body of the device for adjustment of the degree audio/visual signal strength and the time delay of the device so that as a rider becomes more experienced then the device may be set to respond to shorter delays and lighter pressure which may also be set by screw 41. Accordingly, whilst the device is ideally suited for relatively inexperienced riders it can be used to great advantage with greatly experienced riders preparing for particular equestrian competitions where control of the horse's movements are required by the minutest of instructions via the reins, seat, legs and heels of a rider.

Figure 3:
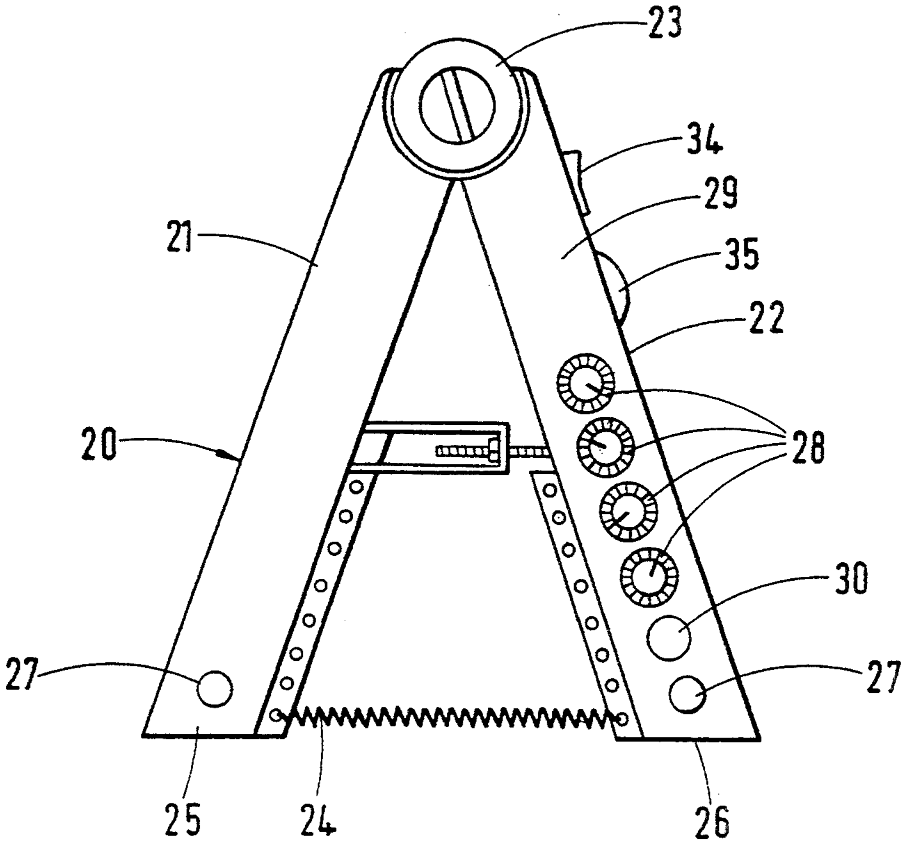
FIG. 3 is one side view of a second indicator device according to the present invention.
Figure 4:
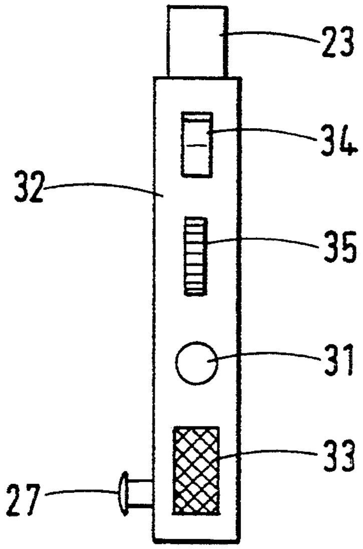
FIG. 4 is another side view of a modified form of the device of FIG. 3.

In an alternative embodiment of a bridle tension indicator device according to the present invention there is provided as shown in FIGS. 3 and 4, a two part housing 20 in which each part 21, 22 is an elongate hollow structure having electrical circuit means, as previously referred to, located therein. The elongate hollow structures 21, 22 are pivotally mounted one relative to the other at one end 23 of each elongate structure and biased into a non operative closed position. Preferably, the biasing force is provided by a spring 24 connected to the elongate structures towards the non connected free ends 25, 26 thereof. The device can in this instance be attached at its free ends 25, 26 by studs 27 to the reins (not shown) with a small loop in the rein to allow some relative opening movement between the two elongate housing structures.

The controls and indicators for the device are located on one elongate housing structure 22. Various time delay audio/visual control knobs 28 associated with scales on the body of the device are located on front face 29 of structure 22 together with a lamp 30 to indicate when the preset time delay is surpassed. A second lamp or opaque window 31 is provided in side surface 32 of structure 22 as shown in FIG. 4 together with an audio reproduction device 33, an on/off switch 34, and a volume control 35.

An adjustable stop mechanism 36 is connected between the pivotally interconnected structures 21, 22 so that structures 21, 22 cannot close beyond the point at which they have been preset. In addition each inner face 37, 38 of each respective structure 21, 22 is provided with a flange 39 having a series of holes 40 therein in which the biasing spring 24 can be selectively engaged to adjust the sensitivity of the device. The operation of the device is otherwise identical to the device of FIGS. 1 and 2 in that the structures move apart until a predetermined pressure level/time delay is reached on the reins and the electrical circuit generates a visual or audio signal.

The principle of the instructing the rider of a horse to correctly control the horse's movement is further advanced by modifying the basic concept of the bridle tensioning device, that is, to provide a signal when a rider's movement is incorrect. It is noted that particularly in equestrian events a rider's posture must also be correct and therefore it is proposed to modify the switching circuit so that it contains a switch which activates the circuit whenever its position is changed from a pre-set horizontal or vertical plane.

This switch device constructed so that a slight movement would be insufficient to activate the mechanism. Moreover, the circuit is provided with a time delay which prevents immediate operation of the circuit after the circuit has been activated to avoid operation of the device upon momentary changes in posture.

The electrical circuit for producing a visual or audible signal is in itself well known and can be identical to that referred to above. Therefore such circuitry will not be discussed further. The circuit can be operated by a switch in the form of a rotary or rolling ball of conductive material, or indeed any other means of closing circuit such as a pre-biased leaf spring, or simply a pendulum switch.

The signal emitted by the electrical circuit can be converted into audio or visual signals with these features so arranged that they may be switched on together or one at a time and the intensity of the signal may be varied as required. The audio signals are preferably produced by a simple buzzer, or a quartz chip. A similar circuit may be incorporated to produce a more sophisticated device. For example, electronically simulated vocal instructions such as "lock up" or any other command depending on that part of the body to which the device is being attached.

In one alternative embodiment according to the invention the indicator device has a two part housing with electronic push button or tough selector switches described for presetting the tension of the device. In addition the indicator device may be permanently connected into a rein with appropriate connections between the device and strap. The indicator device may be attached to one rein in a bridle but there is no reason why the device should not be connected one in each side and to a set of reins. This would be especially useful for people using a double bridle and the devices can be made so that a signal for each individual device would be slightly different thus immediately informing the rider as to whether it was his right hand or his left hand that was at fault or the fingers holding either the bridoon rein or the curb rein.

The constant level indicator is so constructed that it may be worn attached directly onto a person's head, or head gear, on a shoulder, or on any other convenient part of the anatomy. A strap for securing the device is threaded through loops extending from the constant level indicator housing, or alternatively, by way of a clip. In a further alternative form the body of the constant level indicator may be provided with a flexible flange or similar arrangement so that it can be fixed to other parts of the body such as the wrist or forearm and therefore be used as an indicator for a change in position of that part of the body on which it has been placed.

Accordingly, there is provided a constant level indicator which indicates those occasions when the head of a person wearing the device is dropped or raised relative to a horizontal or vertical plane for a period greater than that provided by the time delay set into the electrical circuit.

Whilst the device is particularly useful, for example, to persons riding horses, who lose their correct position by either constantly looking down or raising their hands incorrectly, such a constant level indicator device can find many other uses particularly in the medical field for example where the posture of a person's back can be corrected and the back muscles strengthened.

The constant level indicator may conveniently incorporate a simple computer circuit which could record, for later display and analysis, various movements that have taken place during previous periods of use.

I claim:

1. A bridle tension indicator device suitable for connection to a rein of the bridle of a horse, comprising a housing, attachment means extending from the housing for attaching the device to the rein, an electrical circuit located within the housing being responsive to tension in the rein for producing a signal when the selected tension is exceeded, switch means on the housing for initiating operation of the electrical circuit and indicator means on the housing responsive to said signal for providing an indication that the selected tension is exceeded, whereby excessive tension apt to damage the mouth of the horse is avoided.

2. An indicator device according to claim 1, comprising selector means on the said housing for determining said selected tension.

3. An indicator device according to claim 1, wherein said attachment means are attached to the rein at a spaced location there along, the rein between said spaced locations forming a bight portion wherein the rein is tension free.

4. An indicator device according to claim 1, wherein the housing is in two parts one slidable within the other.

5. An indicator device according to claim 4, wherein each said housing part has an elongate bar extending outwardly therefrom in mutually opposed directions of movement of the two sliding parts.

6. An indicator device according to claim 1, wherein each attachment means comprises a lug having two bars extending transversely therefrom and around which the rein is arranged to be threaded.

7. An indicator device according to claim 6, wherein each lug includes a stud mounted thereon for attaching the rein to the lug.

8. An indicator device according to claim 1, wherein the parts of the housing are biased to a closed position by a spring.

9. An indicator device according to claim 1, comprising attachment means for attaching the device to a person when riding a horse, wherein said electrical circuit is responsive to deviation from a horizontal or vertical plane for producing an electrical signal representative of the said deviation from the horizontal or vertical plane, whereby said indicator provides an indication of a deviation on the said horizontal or vertical plane so that the rider can correct his riding posture.

10. An indicator device as claimed in claim 9, wherein the electrical circuit includes a time delay circuit for preventing operation of the electrical circuit upon momentary deviations of the switch from the horizontal or vertical plane.

11. A bridle tension indicator device suitable for connection to a rein of a bridle for a horse, comprising a housing having two parts one slidable within the other, an elongate bar extending outwardly from the respective housing part in mutually opposed directions of movement of the two sliding parts, each bar being provided with two transverse bars extending therefrom around which a rein is arranged to be threaded, a stud mounted on each bar for attachment of the rein to the bar, an electrical circuit located within the housing and being responsive to tension within the rein for producing a signal when a selected tension is succeeded, switch means on the housing for initiating operation of the electrical circuit, and indicator means on the housing responsive to said signal for providing an indication that the selected tension is exceeded, whereby excessive tension apt to damage the mouth of the horse is avoided.

* * * * *